United States Patent [19]

Lange

[11] 4,386,939

[45] Jun. 7, 1983

[54] REACTION PRODUCTS OF CERTAIN HETEROCYCLES WITH AMINOPHENOLS

[75] Inventor: Richard M. Lange, Euclid, Ohio

[73] Assignee: The Lubrizol Corporation, Wickliffe, Ohio

[21] Appl. No.: 364,287

[22] Filed: Apr. 1, 1982

Related U.S. Application Data

[63] Continuation-in-part of Ser. No. 102,077, Dec. 10, 1979, abandoned.

[51] Int. Cl.$^3$ .............................................. C10L 1/22
[52] U.S. Cl. ............................................. 44/63; 44/74; 44/75; 564/439; 564/369; 564/395; 564/399; 564/440; 564/443
[58] Field of Search ............... 44/63, 74, 75; 564/369, 564/395, 399, 440, 443; 252/51.5 R, 47.5

[56] References Cited

U.S. PATENT DOCUMENTS

| 1,712,716 | 5/1929 | Reddelien et al. | 564/400 |
|---|---|---|---|
| 1,907,444 | 5/1933 | Reddelien et al. | 562/453 |
| 2,859,251 | 11/1958 | Linn | 568/792 |
| 3,868,409 | 2/1975 | Manaka | 560/222 |
| 3,932,288 | 1/1976 | Hoke | 252/33 |
| 3,951,830 | 4/1976 | Karn | 252/78.3 |
| 4,071,327 | 1/1978 | Dorer, Jr. | 44/66 |

FOREIGN PATENT DOCUMENTS 503031  7/1930  Fed. Rep. of Germany .
744757  5/1943  Fed. Rep. of Germany .
744758  5/1943  Fed. Rep. of Germany .
2327982  5/1977  France .

OTHER PUBLICATIONS

Chemical Abstracts 33:5504-05 (1939).
Chemical Abstracts 42:3344e (1948).
Chemical Abstracts 83:58816a (1975).

Primary Examiner—Charles F. Warren
Assistant Examiner—Y. Harris-Smith
Attorney, Agent, or Firm—Ronald L. Lyons; Raymond F. Keller

[57] ABSTRACT

Aminophenols and analogous aromatic compounds, especially those containing a hydrocarbon-based substituent preferably having about 10 to about 750 aliphatic carbon atoms, react with 3- or 4-membered ring heterocyclic compounds, preferably epoxides, to form compositions useful as dispersants and detergents in lubricants and fuels.

37 Claims, No Drawings

REACTION PRODUCTS OF CERTAIN HETEROCYCLES WITH AMINOPHENOLS

This application is a continuation-in-part of copending application Ser. No. 102,077, filed Dec. 10, 1979, now abandoned.

This invention relates to new compositions of matter useful as additives for lubricants and fuels. In its most general sense, the invention comprises certain nitrogen-containing compositions and additive concentrates, lubricants and fuels containing them. The nitrogen-containing compositions are prepared by reacting, at a temperature from about 25° C. to about 250° C.:

(A) at least one aromatic compound having the formula

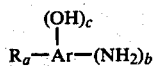

wherein:
Ar is an aromatic radical;
R is hydrogen or a substantially saturated nonaromatic hydrocarbon-based radical; and
each of a, b and c is an integer from 1 to three times the number of aromatic nuclei in Ar; with
(B) at least one 3- or 4-membered ring heterocyclic compound in which the hetero atom is a single oxygen, sulfur or nitrogen atom;
at least about one-half equivalent of reagent B being used per equivalent of reagent A.

Increasing petroleum shortages, spiraling equipment replacement costs and environmental concern have led to increased efforts to find new and effective additives for the treatment of lubricants based on oils of lubricating viscosity (e.g., lubricating oils and greases) and normally liquid fuels (such as gasoline and the like).

A specific example of such efforts is the development of additives for gasoline which promote carburetor cleanliness and reduce blockage of the carburetor due to ice formation during engine start-up. It has long been known that the non-volatile constituents of fuel sometimes form deposits and varnish on sensitive parts in carburetors. It has also been known that highly volatile fuels, such as those used during cold weather, promote the ice formation in narrow carburetor channels due to the cooling effect of fuel evaporation. Such blockage can result in engine stalling and accompanying fuel waste.

In a typical embodiment of this invention, as described below, the inventive compositions serve as carburetor detergent and anti-icing additives and thus aid in improved engine performance and fuel conservation.

It is an object of this invention to provide nitrogen-containing compositions useful as additives for lubricants and fuels.

A further object is to provide additive concentrates for treating fuels and lubricants.

A still further object is to provide fuel and lubricant compositions containing the inventive nitrogen-containing compositions.

Other objects will be apparent upon study of the following disclosure.

As previously mentioned, the nitrogen-containing compositions of this invention are prepared by the reaction of (A) at least one aromatic compound having a specific formula with (B) at least one specifically defined heterocyclic compound. In the formula for reagent A, Ar is an aromatic radical which may be mononuclear or polynuclear and which may or may not (but usually does not) contain hetero atoms such as oxygen, nitrogen or sulfur. Mononuclear aromatic compounds from which Ar may be derived include benzene, pyridine, thiophene, furan and the like. Polynuclear compounds may be of the fused ring type such as naphthalene, anthracene, phenanthrene, indole and carbazole, or the linked ring type such as biphenyl, diphenylmethane, diphenyl oxide, diphenylamine, benzophenone, and diphenyl sulfide and polysulfide. Other suitable Ar radicals are derived from polynuclear compounds containing more than one bridge between the nuclei (e.g., fluorene). The preferred Ar radicals are the single-ring and fused-ring ones containing no linked-ring moieties, especially the single-ring ones and more especially the carbocyclic ones.

In the same formula, R is hydrogen or a substantially saturated non-aromatic hydrocarbon-based radical, preferably the latter. As used herein, the term "substantially saturated" means that the radical contains no more than one carbon-to-carbon double bond for every 10 carbon-to-carbon single bonds. The term "non-aromatic hydrocarbon-based radical" denotes a non-aromatic radical having a carbon atom directly attached to the remainder of the molecule and having predominantly hydrocarbon character within the context of this invention. Such radicals include the following:

(1) Hydrocarbon radicals; that is, aliphatic (e.g., alkyl or alkenyl) or alicyclic (e.g., cycloalkyl or cycloalkenyl) radicals.

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents; examples are hydroxy, halo, carbalkoxy, nitro and sulfonic acid ester substituents.

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

The R radical usually has an average of about 10 to about 750 aliphatic carbon atoms. Most often, it is an aliphatic hydrocarbon radical and especially an alkyl or alkenyl radical having an average of about 12 to about 400 carbon atoms and desirably at least about 30 carbon atoms. Many suitable R radicals are derived from polymers (both homopolymers and interpolymers) of $C_{2-10}$ olefins such as ethylene, propylene, 1-butene, isobutene, butadiene and the like. Polymers of 1-monoolefins, and especially of butene mixtures comprising predominantly isobutene, are preferred. The R radical can also be derived from a halogenated (usually chlorinated or brominated and especially chlorinated) polymer of this type. Other suitable sources of the R radical are monomeric high molecular weight alkenes such as 1-tetracontene and chlorinated derivatives thereof, and aliphatic petroleum fractions such as paraffin waxes, white oils, and the like. The most preferred R radicals are alkyl and monoalkenyl radicals.

As will be apparent from the above formula, reagent A contains at least one each of the R, hydroxy and amino groups. They may contain more than one of any or all of these groups, the upper limit being a situation in which any one or more of the subscripts a, b and c is equal to 3 times the number of aromatic nuclei in Ar. Usually, however, each of a and c is 1 and b is 1 or 2, most often also 1. Thus, the preferred aminophenols are those derived from a monoalkylated mononuclear aminophenol. In most of such compounds, R is ortho or (usually) para to the hydroxy group.

Reagent A may also contain other substituents on the aromatic ring, and it is to be understood that the symbol Ar denotes compounds which contain either hydrogen or such other substituents attached to appropriate ring atoms, whether carbon or hetero atoms. Suitable other substituents include alkyl, alkoxy, halo, cyano, alkylamino, dialkylamino, carbalkoxy and hydroxyalkyl. The alkyl groups in such subsituents are preferably lower alkyl groups; that is, alkyl groups containing up to 7 carbon atoms. The maximum number of such other substituents in reagent A is 3. Most often, however, no such substituents are present.

Compounds useful as reagent A are known to those skilled in the art. They include the alkylated aminophenols and similar compounds disclosed in U.S. Pat. Nos. 4,320,020 and 4,320,021, which are incorporated by reference herein for such disclosures.

Reagent B, as previously noted, is at least one 3- or 4-membered ring heterocyclic compound in which the hetero atom is a single oxygen, sulfur or nitrogen atom. Such compounds include epoxides, episulfides and aziridines comprising 3-membered rings, and oxetanes, thietanes and azetidines comprising 4-membered rings. Illustrative compounds of this type are ethylene oxide, propylene oxide, the butene oxides, epichlorohydrin, glycidol, styrene oxide, ethylene sulfide, propylene sulfide, ethyleneimine, N-ethyl ethyleneimine, propyleneimine, oxacyclobutane, thiacyclobutane and azacyclobutane. The preferred compounds are those in which the hetero atom is oxygen and especially the epoxides; ethylene oxide and propylene oxide are particularly preferred because of their availability.

The reaction between reagents A and B is typically carried out at a temperature from about 25° C. to about 250° C., preferably from about 30° C. to about 150° C. It can be carried out under pressure if either reagent is a gas (e.g., when ethylene oxide or propylene oxide is used as reagent B).

In some instances, it may be preferable to facilitate the reaction by using a catalyst, typically a basic catalyst. Illustrative catalysts are the alkali metal and alkaline earth metal oxides, hydroxides and alkoxides illustrated by sodium hydroxide, lithium hydroxide, potassium hydroxide, calcium hydroxide and magnesium methoxide.

At least about ½ equivalent and generally not more than about 20 equivalents of reagent B are used per equivalent of reagent A. Most often, the ratio of equivalents of reagent B to reagent A is between about 1:1 and about 10:1. When a catalyst is used, it is ordinarily present in an amount ranging from about 0.1 to about 10 mole percent of reagent B. For the purposes of this invention, the equivalent weight of reagent A is its molecular weight divided by the number of amino or hydroxy hydrogen atoms therein, and the equivalent weight of reagent B is its molecular weight divided by the number of hetero atoms therein.

The reaction is normally effected in the presence of a substantially inert, normally liquid organic diluent such as mineral oil, stoddard solvent, textile spirits or petroleum naphtha. Following the reaction, the product may be isolated by standard techniques; however, isolation is frequently unnecessary as the product may often be used in solution in the diluent employed.

The nitrogen-containing compositions of this invention are generally mixtures of chemical compounds which may be completely described only in terms of the method for their preparation. It is known, however, that they contain compounds having the formula

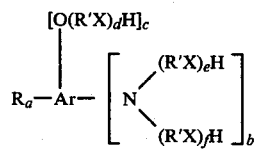

wherein:
Ar, R, a b and c are as previously defined;
R' is a divalent 1,2- or 1,3-hydrocarbon-based radical;
X is oxygen, sulfur or NR";
R" is hydrogen or a hydrocarbon-based radical containing from 1 to about 18 carbon atoms;
each of d, e and f is an integer from 0 to 10; and
d+e+f is at least 1.

Most often, R' is a 1,2 radical and X is oxygen.

The preparation of the compounds of this invention is illustrated by the following examples. All parts and percentages are by weight.

EXAMPLE 1

Glycidol, 32 parts (0.43 equivalent), was added slowly at about 75° C. to 554 parts of a solution in mineral oil of a hydrocarbon-substituted aminophenol in which the substituent was derived from a polybutene comprising predominantly isobutene units and having a number average molecular weight of about 1,000 as determined by vapor phase osmometry (more fully described in Example 3B of U.S. Pat. No. 4,320,020). The reaction mixture was heated at 120° C. for 3½ hours, vacuum stripped at the same temperature, cooled and filtered through diatomaceous earth. The filtrate was a mineral oil solution of the desired nitrogen-containing composition.

EXAMPLE 2

Gaseous ethylene oxide, 66 parts, was passed over 2 hours at 150° C. into 1,336 parts of the substituted aminophenol solution of Example 1. The mixture was purged with nitrogen at 150° C. for 3 hours; an additional 16 parts of ethylene oxide was then added and nitrogen purging was continued for 2 hours. The mixture became gel-like when cooled; it was diluted with 599 parts of mineral oil at 100° C. and the product was an oil solution of the desired composition containing 0.34% nitrogen.

EXAMPLE 3

Ethylene oxide, 75 parts, was passed at 95° C. into 935 parts of a solution in mineral oil of a substituted aminophenol similar to that of Example 1 (more fully described in Example 2 of British Pat. No. 1,567,828). The reaction mixture was vacuum stripped; the residue was an oil solution of the desired nitrogen-containing composition.

EXAMPLE 4

Propylene oxide, 35 parts, was added over 1½ hours at 100° C. to 813 parts of the substituted aminophenol solution of Example 3. The mixture was heated for 2 hours at 100° C., an additional 20 parts of propylene oxide was added and heating was continued for 1½ hours. The mixture was vacuum stripped and filtered through diatomaceous earth; the filtrate was an oil solution of the desired nitrogen-containing composition.

EXAMPLE 5

Propylene oxide, 44 parts, was added over 2 hours at 95° C. to 842 parts of the substituted aminophenol solution of Example 1. The mixture was heated at 115° C. for 5 hours, vacuum stripped and filtered through diatomaceous earth. The filtrate was a mineral oil solution of the desired nitrogen-containing composition.

EXAMPLE 6

Following the procedure of Example 5, a product was prepared from 600 parts of the substituted aminophenol solution of Example 1 and 10 parts of propylene oxide.

EXAMPLE 7

Glycidol, 11.5 parts, was added over ¼ hour at 95° C. to 100 parts of a 50% solution in mineral oil (containing 3.76% nitrogen) of a tetrapropene-substituted aminophenol. The mixture was heated for 5 hours at 135° C.; the product was a mineral oil solution of the desired composition containing 2.76% nitrogen.

EXAMPLE 8

A mixture of 570 parts of the tetrapropene-substituted aminophenol of Example 7, 2.85 parts of potassium hydroxide and 350 parts of toluene was cooled in a mixture of acetone and solid carbon dioxide as 44 parts of ethylene oxide was added, with stirring. The mixture was allowed to stand at room temperature for about 200 hours and was then vacuum stripped and filtered through diatomaceous earth. The filtrate was a mineral oil solution of the desired composition containing 3.82% nitrogen.

EXAMPLE 9

Following substantially the procedure of Example 8, a nitrogen-containing composition was prepared from 106 parts of ethylene oxide, 1,911 parts of the substituted aminophenol solution of Example 3, and 0.1 part of lithium hydroxide monohydrate.

EXAMPLE 10

Propylene oxide, 64 parts, was added over 1½ hours at 95° C. to 3,005 parts of the substituted aminophenol solution of Example 3. The mixture was heated for 6 hours at 100° C., vacuum stripped and filtered while hot through diatomaceous earth. The filtrate was a mineral oil solution of the desired nitrogen-containing composition.

As previously indicated, the nitrogen-containing compositions of this invention are useful as additives for lubricants, in which they function primarily as dispersants and detergents. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. The compositions can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the nitrogen-containing compositions of this invention.

Natural oils include liquid petroleum oils and solvent-treated or acid-treated mineral lubricating oils of the paraffinic, naphthenic and mixed paraffinic-naphthenic types. Oils of lubricating viscosity derived from coal or shale are also useful base oils.

Synthetic lubricating oils include hydrocarbon oils and halo-substituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes)]; alkylbenzenes [e.g., dodecylbenzenes, tetradecylbenzenes, dinonylbenzenes, di(2-ethylhexyl)benzenes]; polyphenyls (e.g., biphenyls, terphenyls, alkylated polyphenols); and alkylated diphenyl ethers and alkylated diphenyl sulfides and the derivatives, analogs and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol and tripentaerythritol.

Silicon-based oils such as the polyalkyl-, polyaryl-, polyalkoxy-, or polyaryloxysiloxane oils and silicate oils comprise another useful class of synthetic lubricants;

they include tetraethyl silicate, tetraisopropyl silicate, tetra-(2-ethylhexyl) silicate, tetra-(4-methyl-2-ethylhexyl) silicate, tetra-(p-tert-butylphenyl) silicate, hexa-(4-methyl-2-pentoxy)disiloxane, poly(methyl)siloxanes and poly(methylphenyl)siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined and rerefined oils can be used in the lubricants of the present invention. Unrefined oils are those obtained directly from a natural or synthetic source without further purification treatment. For example, a shall oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration and percolation are known to those skilled in the art. Rerefined oils are obtained by processes similar to those used to obtain refined oils applied to refined oils which have been already used in service. Such rerefined oils are also known as reclaimed or reprocessed oils and often are additionally processed by techniques for removal of spent additives and oil breakdown products.

Generally, the lubricants of the present invention contain an amount of the composition of this invention sufficient to disperse insoluble impurities such as engine sludge. Normally this amount will be about 0.01% to about 20% by weight.

The invention also contemplates the use of other additives in lubricants in combination with the nitrogen-containing compositions. Such additives include, for example, auxiliary detergents and dispersants of the ash-producing or ashless type, corrosion- and oxidation-inhibiting agents, pour point depressing agents, extreme pressure agents, color stabilizers and anti-foam agents.

The ash-producing detergents are exemplified by oil-soluble neutral and basic salts of alkali or alkaline earth metals with sulfonic acids, carboxylic acids, and organic phosphorus acids characterized by at least one direct carbon-to-phosphorus linkage including those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature about 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenols, thiophenol, sulfurized alkylphenols, and condensation products of formaldehyde with phenolic substances; alcohols such as methanol, 2-propanol, octyl alcohol, Cellosolve, Carbitol, ethylene glycol, stearyl alcohol and cyclohexyl alcohol; and amines such as aniline, phenylenediamine, phenothiazine, phenyl-$\beta$-naphthylamine and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Auxiliary ashless detergents and dispersants are so colled despite the fact that, depending on its constitution, the dispersant may upon combustion yield a nonvolatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogent-containing compounds such as amine, organic hydroxy compounds such as phenols and alcohols, and/or basic inorganic materials. Examples of these "carboxylic dispersants" are described in many U.S. patents including U.S. Pat. Nos. 3,272,746; 3,381,022; and 4,234,435.

(2) Reaction products of relatively high molecular weight aliphatic or alicyclic halides with amines, preferably polyalkylene polyamines. These may be characterized as "amine dispersants" and examples thereof are described for example, in U.S. Pat. Nos. 3,275,554; 3,438,757; 3,454,555; and 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in U.S. Pat. Nos. 3,368,972; 3,413,347; and 3,980,569 are illustrative.

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in a number of U.S. patents.

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in U.S. Pat. Nos. 3,329,658; 3,449,250; 3,519,565; 3,666,730; 3,687,849; and 3,702,300.

All of the above-noted patents are incorporated by reference herein for their disclosures of ashless dispersants.

Extreme pressure agents and corrosion- and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl oleate, sulfurized alkylphenols, sulfurized dipentene, and sulfurized terpenes; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite and diisobutyl-substituted phenyl phosphite; metal thiocarbamates such as zinc dioctyldithiocarbamate and barium heptylphenyl dithiocarbamate; Group II metal phosphorodithioates such as zinc dicyclohexylphosphorodithioate, zinc dioctylphosphorodithioate, barium di(heptylphenyl)phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The nitrogen-containing compositions of this invention can also be used in fuels where they function as carburetor detergents and deposit reducers. Fuel compositions of the invention contain a major proportion of a normally liquid fuel, usually a hydrocarbonaceous petroleum distillate fuel such as motor gasoline as defined by ASTM Specification D439 and diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain an amount of the nitrogen-containing composition of this invention sufficient to provide it with dispersant, detergent or demulsifying properties; usually this amount is about 0.1 to about 10,000 parts by weight, preferably about 10 to 1000 parts, of the composition of this invention per million parts of fuel.

The fuel compositions of this invention can contain, in addition to the nitrogen-containing composition, other additives which are well known to those of skill in the art. These include antiknock agents, deposit preventers or modifiers such as triaryl phosphates, dyes, cetane improvers, antioxidants such as 2,6-di-tertiary-butyl-4-methylphenol, rust inhibitors such as alkylated succinic acids and anhydrides, bacteriostatic agents, gum inhibitors, metal deactivators, demulsifiers, upper cylinder lubricants and anti-icing agents.

In a preferred fuel composition of this invention, the nitrogen-containing composition is combined with an auxiliary ashless dispersant in gasoline. Suitable ashless dispersants include esters of mono- or polyols and high molecular weight mono- or polycarboxylic acid acylating agents containing at least 30 carbon atoms in the acyl moiety. Such esters are well known to those skilled in the art. See, for example, French Pat. No. 1,396,645; British Pat. Nos. 981,850; 1,055,337 and 1,306,529; and U.S. Pat. Nos. 3,255,108; 3,311,558; 3,331,776; 3,346,354; 3,522,179; 3,579,450; 3,542,680; 3,381,022; 3,639,242; 3,697,428 and 3,708,522. These patents are expressly incorporated herein by reference for their disclosure of suitable esters and methods for their preparation.

In another preferred embodiment, the nitrogen-containing composition of this invention is used in conjunction with a borated alkenylsuccinic acid-polyamine dispersant/detergent. Such borated materials are known to the art; see, for example, U.S. Pat. No. 3,087,936 which is hereby incorporated by reference for its disclosure of borated materials. Generally, the weight ratio of the nitrogen-containing composition to either of the aforesaid dispersants is from about 0.1:1 to about 10:1, preferably from about 1:1 to about 10:1.

In still other embodiments of this invention, the nitrogen-containing composition can be combined with Mannich condensation products formed from substituted phenols, aldehydes, polyamines and aminopyridines for use in lubricants or fuels. Such condensation products are described in U.S. Pat. Nos. 3,649,659; 3,558,743; 3,539,633; 3,704,308; and 3,724,277.

The nitrogen-containing compositions can be added directly to the fuel or lubricating oil to form the fuel and lubricant compositions of this invention or they can be diluted with a substantially inert, normally liquid organic diluent such as mineral oil, xylene, alcohol, nitroalkane, chloroalkane or normally liquid fuel to form an additive concentrate which is then added to the fuel or lubricating oil. These concentrates generally contain about 20 to about 80 percent of the nitrogen-containing composition of this invention and can contain in addition any of the above-described conventional additives, particularly the aforedescribed ashless dispersants in the aforesaid proportions.

What is claimed is:

1. A nitrogen-containing composition prepared by reacting, at a temperature from about 25° C. to about 250° C.:

(A) at least one aromatic compound having the formula

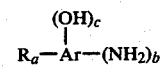

wherein:
Ar is a single-ring or fused-ring aromatic radical;
R is a substantially saturated non-aromatic hydrocarbon-based radical containing an average of about 10 to about 750 aliphatic carbon atoms; and
each of a, b and c is an integer from 1 to three times the number of aromatic nuclei in Ar; with
(B) at least one 3- or 4-membered ring heterocyclic compound in which the heterocyclic atom is a single oxygen, sulfur or nitrogen atom;
at least about one-half equivalent of reagent B being used per equivalent of reagent A.

2. A composition according to claim 1 wherein R is a hydrocarbon-based radical.

3. A composition according to claim 2 wherein Ar is a single-ring radical and a is 1.

4. A composition according to claim 3 wherein R is an aliphatic hydrocarbon radical.

5. A composition according to claim 4 wherein R is an alkyl or monoalkenyl radical having an average of about 12 to about 400 carbon atoms.

6. A composition according to claim 5 wherein R is derived from a polymer of at least one $C_{2-10}$ olefin and contains an average of at least about 30 carbon atoms.

7. A composition according to claim 6 wherein Ar is a benzene ring and each of b and c is 1 or 2.

8. A composition according to claim 7 wherein R is a polybutenyl radical comprising predominantly isobutene groups.

9. A composition according to claim 3 wherein the heterocyclic atom in reagent B is oxygen.

10. A composition according to claim 9 wherein reagent B is an epoxide.

11. A composition according to claim 10 wherein b and c are each 1 and R is para to the hydroxy group.

12. A composition according to claim 11 wherein R is an aliphatic hydrocarbon radical.

13. A composition according to claim 12 wherein R is an alkyl or monoalkenyl radical having an average of about 12 to about 400 carbon atoms.

14. A composition according to claim 13 wherein R is derived from a polymer of at least one $C_{2-10}$ olefin and contains an average of at least about 30 carbon atoms.

15. A composition according to claim 14 wherein Ar is a benzene ring and each of b and c is 1 or 2.

16. A composition according to claim 15 wherein R is a polybutenyl radical comprising predominantly isobutene groups.

17. A composition according to claim 16 wherein reagent B is ethylene oxide or propylene oxide.

18. A composition according to claim 17 wherein about 1 to about 10 equivalents of reagent B is used per equivalent of reagent A.

19. A nitrogen-containing composition having the formula

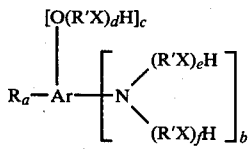

wherein:
Ar is a single-ring or fused-ring aromatic radical;
R is a substantially saturated non-aromatic hydrocarbon-based radical containing an average of about 10 to about 750 aliphatic carbon atoms;
R' is a divalent 1,2- or 1,3-hydrocarbon-based radical;
X is oxygen, sulfur or NR'';
R'' is hydrogen or a hydrocarbon-based radical containing from 1 to about 18 carbon atoms;

each of a, b and c is an integer from 1 to three times the number of aromatic nuclei in Ar;
each of d, e and f is an integer from 0 to 10; and
d+e+f is at least 1.

20. A composition according to claim 19 wherein R is a hydrocarbon-based radical.

21. A composition according to claim 20 wherein Ar is a single-ring radical and a is 1.

22. A composition according to claim 21 wherein R is an aliphatic hydrocarbon radical.

23. A composition according to claim 22 wherein R is an alkyl or monoalkenyl radical having an average of about 12 to about 400 carbon atoms.

24. A composition according to claim 23 wherein R is derived from a polymer of at least one $C_{2-10}$ olefin and contains an average of at least about 30 carbon atoms.

25. A composition according to claim 24 wherein Ar is a benzene ring and each of b and c is 1 or 2.

26. A composition according to claim 25 wherein R is a polybutenyl radical comprising predominantly isobutene groups.

27. A composition according to claim 21 wherein X is oxygen.

28. A composition according to claim 27 wherein R' is a 1,2 radical.

29. A composition according to claim 28 wherein b and c are each 1 and R is para to the hydroxy group.

30. A composition according to claim 29 wherein R is an aliphatic hydrocarbon radical.

31. A composition according to claim 30 wherein R is an alkyl or monoalkenyl radical having an average of about 12 to about 400 carbon atoms.

32. A composition according to claim 31 wherein R is derived from a polymer of at least one $C_{2-10}$ olefin and contains an average of at least about 30 carbon atoms.

33. A composition according to claim 32 wherein Ar is a benzene ring and each of b and c is 1 or 2.

34. A composition according to claim 33 wherein R is a polybutenyl radical comprising predominantly isobutene groups.

35. A composition according to claim 34 wherein R' is an ethylene or propylene radical.

36. An additive concentrate comprising a substantially inert, normally liquid organic diluent and about 20–90% by weight of a nitrogen-containing composition according to claim 1, 3, 7, 8, 9, 15, 16, 17, 19, 21, 25, 26, 27, 33, 34 or 35.

37. A fuel composition comprising a major amount of a normally liquid fuel and about 0.1 to about 10,000 parts by weight, per million parts of said fuel, of a nitrogen-containing composition according to claim 1, 3, 7, 8, 9, 15, 16, 17, 19, 21, 25, 26, 27, 33, 34 or 35.

* * * * *